(12) United States Patent
Wang et al.

(10) Patent No.: US 12,064,531 B2
(45) Date of Patent: Aug. 20, 2024

(54) PRE-LOADABLE DRIED BIOLOGICAL HEART VALVE AND PREPARATION METHOD THEREOF

(71) Applicants: VENUS MEDTECH (HANGZHOU), INC., Zhejiang (CN); Sichuan University, Chengdu (CN)

(72) Inventors: Yunbing Wang, Chengdu (CN); Yang Lei, Chengdu (CN); Gaocan Li, Chengdu (CN); Li Yang, Chengdu (CN); Hou-Sen Lim, Singapore (SG); Dajun Kuang, Zhejiang (CN); Jincheng Yu, Hangzhou (CN)

(73) Assignees: VENUS MEDTECH (HANGZHOU), INC., Hangzhou (CN); Sichuan University, Chengdu (CN)

( * ) Notice: Subject to any disclaimer, the term of this patent is extended or adjusted under 35 U.S.C. 154(b) by 599 days.

(21) Appl. No.: 17/313,877

(22) Filed: May 6, 2021

(65) Prior Publication Data
US 2021/0260247 A1    Aug. 26, 2021

Related U.S. Application Data

(63) Continuation of application No. PCT/CN2019/105345, filed on Sep. 11, 2019.

(51) Int. Cl.
*A61L 27/50* (2006.01)
*A61F 2/02* (2006.01)
*A61F 2/24* (2006.01)
*A61L 27/36* (2006.01)

(52) U.S. Cl.
CPC ....... *A61L 27/3687* (2013.01); *A61L 27/3625* (2013.01); *A61L 27/3641* (2013.01); *A61L 2430/20* (2013.01)

(58) Field of Classification Search
CPC ............ A61F 2/2412; A61F 2210/0004; A61F 2/2415; A61F 2250/0067; A61F 2/24; A61F 2/02; A61F 2240/001; A61L 27/3625
See application file for complete search history.

(56) References Cited

U.S. PATENT DOCUMENTS

| | | | |
|---|---|---|---|
| 4,755,593 A * | 7/1988 | Lauren | A61K 35/12 602/50 |
| 5,782,931 A | 7/1998 | Baxter | |
| 6,132,986 A * | 10/2000 | Pathak | G01N 1/30 435/40.52 |
| 6,156,531 A * | 12/2000 | Pathak | A61L 27/38 435/40.52 |
| 6,177,514 B1 * | 1/2001 | Pathak | A61L 27/3625 600/36 |
| 6,193,749 B1 * | 2/2001 | Schroeder | A61L 27/50 623/1.48 |
| 6,210,440 B1 * | 4/2001 | Stone | A61L 27/3691 623/901 |
| 6,254,635 B1 * | 7/2001 | Schroeder | A61L 27/047 623/23.72 |
| 6,258,320 B1 * | 7/2001 | Persing | A01N 1/00 422/527 |
| 6,290,991 B1 * | 9/2001 | Roser | A61K 9/0021 424/501 |
| 6,312,474 B1 * | 11/2001 | Francis | A61L 27/3687 623/23.72 |
| 6,322,994 B1 * | 11/2001 | Reid | C12N 1/04 435/284.1 |
| 6,383,732 B1 * | 5/2002 | Stone | A61L 27/3691 435/325 |
| 6,479,079 B1 * | 11/2002 | Pathak | A61L 27/3604 424/569 |
| 6,506,339 B1 * | 1/2003 | Girardot | A61L 2/18 435/1.1 |
| 6,534,004 B2 * | 3/2003 | Chen | A61L 2/08 422/1 |
| 6,653,062 B1 * | 11/2003 | DePablo | A01N 1/0221 435/1.3 |
| 6,696,074 B2 * | 2/2004 | Dai | A61K 35/34 435/395 |
| 6,878,168 B2 * | 4/2005 | Carpentier | B65B 63/08 8/94.11 |
| 6,933,326 B1 * | 8/2005 | Griffey | A61L 31/005 523/113 |
| 7,354,749 B2 * | 4/2008 | Fisher | A61L 27/3687 424/94.2 |
| 7,972,376 B1 * | 7/2011 | Dove | A61F 2/2412 435/1.1 |
| 8,748,490 B2 | 6/2014 | Dove et al. | |
| 9,918,832 B2 * | 3/2018 | Tian | A01N 1/0215 |
| 11,517,428 B2 * | 12/2022 | Shang | A61F 2/2436 |

(Continued)

FOREIGN PATENT DOCUMENTS

| | | |
|---|---|---|
| CN | 104334121 A | 2/2015 |
| CN | 105194733 A | 12/2015 |
| CN | 105326581 A | 2/2016 |
| CN | 105963783 A | 9/2016 |
| CN | 106913909 A | 7/2017 |

OTHER PUBLICATIONS

International Search Report and Opinion dated Nov. 27, 2019 for corresponding PCT Application No. PCT/CN2019/105345.

*Primary Examiner* — Seema Mathew
(74) *Attorney, Agent, or Firm* — Raymond Sun

(57) ABSTRACT

A pre-loadable dried biological heart valve and a preparation method thereof. The preparation method includes: Step A: soaking a fresh animal pericardium in an aqueous solution of soluble elastin or glycosaminoglycan, and then subjecting the pericardium to a first cross-linking reaction in a mixed solution of carbodiimide or N-hydroxysuccinimide to allow the soluble elastin or glycosaminoglycan to bind to the pericardium via a chemical bond; and Step B: subjecting the pericardium after the first cross-linking to a second cross-linking reaction in an aqueous glutaraldehyde solution, and then drying the pericardium after the second cross-linking, to obtain the pre-loadable dried biological heart valve. The dried biological heart valve obtained by the above preparation method has good toughness, and is rapidly flattened out in a simulated folding and pressing test.

13 Claims, No Drawings

(56) References Cited

U.S. PATENT DOCUMENTS

| | | | |
|---|---|---|---|
| 11,673,974 B2* | 6/2023 | Awasthi | A61L 26/0023 424/429 |
| 2001/0000804 A1* | 5/2001 | Goldstein | A61L 27/3604 623/23.72 |
| 2003/0035843 A1* | 2/2003 | Livesey | A61K 39/12 424/549 |
| 2004/0158320 A1* | 8/2004 | Simionescu | A61F 2/2412 623/2.14 |
| 2005/0163818 A1* | 7/2005 | Sung | A61L 27/54 424/423 |
| 2006/0177426 A1* | 8/2006 | Gibson | A01N 1/0278 435/284.1 |
| 2006/0204445 A1* | 9/2006 | Atala | A61K 47/6923 424/423 |
| 2006/0217805 A1* | 9/2006 | Dove | A61L 27/3604 623/7 |
| 2007/0292459 A1* | 12/2007 | Cooper | A61K 8/26 424/401 |
| 2008/0195230 A1* | 8/2008 | Quijano | A61B 17/3203 623/23.72 |
| 2008/0302372 A1* | 12/2008 | Davidson | A61L 27/3691 8/94.11 |
| 2014/0377737 A1* | 12/2014 | Kim | A61L 27/26 435/1.1 |
| 2018/0133365 A1* | 5/2018 | Dong | A61L 27/3625 |
| 2020/0038193 A1* | 2/2020 | Li | A61L 27/3683 |
| 2022/0195387 A1* | 6/2022 | Sharfstein | D01D 5/0076 |
| 2022/0288276 A1* | 9/2022 | Batt | C08H 1/06 |
| 2022/0296779 A1* | 9/2022 | Tian | A61L 27/3625 |
| 2022/0331488 A1* | 10/2022 | Ogle | A61L 27/3691 |
| 2022/0346926 A1* | 11/2022 | Sengun | A61F 2/0811 |
| 2023/0347024 A1* | 11/2023 | Thoebe | A61F 2/07 |

* cited by examiner

PRE-LOADABLE DRIED BIOLOGICAL HEART VALVE AND PREPARATION METHOD THEREOF

TECHNICAL FIELD

The present disclosure relates to the field of medical materials and medical devices, and in particular to a pre-loadable dried biological heart valve and a preparation method thereof.

BACKGROUND

Heart valve disease is a common valve regenerative disease. Anatomically it is manifested as narrowing of the blood passage or valvular insufficiency. The treatment of heart valve disease includes thoracotomic valve replacement and percutaneous heart valve replacement. Thoracotomy relates to huge trauma, high risk and slow recovery, and demands the support of extracorporeal circulation, which is intolerable to many patients. Percutaneous heart valve replacement becomes the main trend of valve replacement surgery in the future because of its minor trauma and low risk. Biological heart valve refers to a biomedical material used to replace diseased heart valves in humans. The biological heart valve is generally prepared from porcine pericardium or bovine pericardium, etc. crosslinked by glutaraldehyde.

The interventional biological valves in prior art are generally crosslinked by glutaraldehyde, then sewn on a metal stent, and preserved in a glutaraldehyde solution. Before the interventional valve replacement, it needs to be washed many times, crimped and assembled. This preparation process is cumbersome and easily leads to increased additional risks in surgery. The biological valve which has been preserved in the glutaraldehyde solution for a long time is more prone to contain residual glutaraldehyde which increases the calcification and toxicity of the biological valve. Moreover, the preservation in glutaraldehyde requires washing when used at the operation site. After washing, it is crimped and loaded into a delivery system at the operation site, which virtually increases the operation time. Therefore, the development of biological valve in the form of a dried valve preserved without a glutaraldehyde solution and pre-crimped and loaded into a valve delivery system can better solve the above problems. However, the dried biological valve pre-loaded in the valve delivery system has to withstand a long time of mechanical crimping and is prone to crimping damage. Therefore, greater demand for the toughness of the biological valve in the dried loaded state is raised. The existing biological valve is still insufficient in toughness.

Therefore, the existing technology still needs to be improved and developed.

SUMMARY

In view of the above-mentioned shortcomings existing in the prior art, an objective of the present disclosure is to provide a pre-loadable dried biological heart valve and a preparation method thereof, to solve the problem that biological valves in prior art needs to be preserved in a glutaraldehyde solution, cannot be pre-loaded in a delivery system, and requires washing, crimping, and assembling in site; and has insufficient toughness.

The following technical solution adopted in the present disclosure is as follows.

The present disclosure provides a method for preparing a pre-loadable dried biological heart valve, which includes:

Step A: soaking a fresh animal pericardium in an aqueous solution of soluble elastin or glycosaminoglycan, and then subjecting the pericardium to a first cross-linking reaction in a mixed solution of carbodiimide or N-hydroxysuccinimide to allow the soluble elastin or glycosaminoglycan to bind to the pericardium via a chemical bond; and Step B: subjecting the pericardium after the first cross-linking to a second cross-linking reaction in an aqueous glutaraldehyde solution, and then drying the pericardium after the second cross-linking, to obtain the pre-loadable dried biological heart valve.

The carboxyl group contained in the elastin or glycosaminoglycan can be chemically cross-linked with the amino group in the fresh pericardium in the mixed solution of carbodiimide or N-hydroxysuccinimide to form an amide bond after dehydration condensation. In this way, the elastin or glycosaminoglycan is bound to the pericardium via a chemical bond, whereby the toughness of the biological valve is improved to avoid the mechanical crimping caused by being in a compressed state for a long time after the heart valve is crimped and loaded.

According to the method for preparing a pre-loadable dried biological heart valve, in Step A, the pericardium is soaked for 2 to 24 hrs in a 0.1 to 10 wt % aqueous solution of soluble elastin or glycosaminoglycan at 25 to 37° C. with shaking.

According to the method for preparing a pre-loadable dried biological heart valve, in Step A, the pericardium is subjected to the first cross-linking reaction by soaking in a 0.1 to 1 M mixed solution of carbodiimide or N-hydroxysuccinimide at 25 to 37° C. with shaking for 2 to 24 hrs.

According to the method for preparing a pre-loadable dried biological heart valve, in Step B, the pericardium after the first cross-linking is subjected to cross-linking reaction by soaking in a 0.25 to 1 vol % aqueous glutaraldehyde solution at 25 to 37° C. with shaking for 1 to 7 days.

According to the method for preparing a pre-loadable dried biological heart valve, in Step B, the drying is dehydration and drying in an alcohol solvent.

According to the method for preparing a pre-loadable dried biological heart valve, in Step B, the pericardium after the second cross-linking is dehydrated and dried over gradient concentrations of an alcohol solvent.

According to the method for preparing a pre-loadable dried biological heart valve, in Step B, the alcohol solvent includes one or more of methanol, ethanol, isopropanol, glycerol, n-propanol, n-butanol, n-pentanol, n-undecanol, n-dodecanol, 2-propanol, 2-butanol, 2-hexanol, cyclohexanol, and tert-butanol.

According to the method for preparing a pre-loadable dried biological heart valve, in Step B, the pericardium after the secondary crosslinking is sequentially soaked in 50% isopropanol or 50% glycerol for 20 to 30 hrs and then in 90% isopropanol or 10% glycerol for 20 to 30 hrs at 25 to 37° C. to accomplish the dehydration and drying.

According to the method for preparing a pre-loadable dried biological heart valve, in Step A, the soluble elastin or glycosaminoglycan solution is selected from a group consisting of: soluble elastin, hyaluronic acid, chondroitin sulfate, dermatan sulfate, keratan sulfate, heparan sulfate, heparin, and a mixture of any combination thereof.

According to the method for preparing a pre-loadable dried biological heart valve, in Step A, the method further includes a step of washing the fresh animal pericardium before soaking the fresh animal pericardium in the aqueous solution of soluble elastin or glycosaminoglycan.

According to the method for preparing a pre-loadable dried biological heart valve, the step of washing the fresh animal pericardium includes washing the fresh animal pericardium with distilled water at 3 to 5° C. with shaking at 80 to 120 rpm for 1.5 to 3 hrs.

According to the method for preparing a pre-loadable dried biological heart valve, the step of washing the fresh animal pericardium includes a cell removal treatment.

The present disclosure also provides a pre-loadable dried biological heart valve, which is prepared by the preparation method as described above.

Beneficial effects: The present disclosure provides a pre-loadable dried biological heart valve and a preparation method thereof. The dried biological heart valve prepared by the preparation method of the present disclosure has good toughness and can be quickly flattened in a simulated folding and pressing test.

DESCRIPTION OF THE EMBODIMENTS

The present disclosure provides a pre-loadable dried biological heart valve and a preparation method thereof. To make the object, technical solution and effect of the present disclosure clearer, the present disclosure will be described in further detail below. It should be understood that the specific examples described herein are merely provided for illustrating, but not to limit the present disclosure.

A preferred embodiment of the present disclosure provides a method for preparing a pre-loadable dried biological heart valve, that is, a method for toughening a pre-loadable dried biological heart valve, which includes:

Step S100: soaking a fresh animal pericardium in an aqueous solution of soluble elastin or glycosaminoglycan, and then subjecting the pericardium to a first cross-linking reaction in a mixed solution of carbodiimide or N-hydroxysuccinimide to allow the soluble elastin or glycosaminoglycan to bind to the pericardium via a chemical bond; and Step S200: subjecting the pericardium after the first cross-linking to a second cross-linking reaction in an aqueous glutaraldehyde solution, and then drying the pericardium after the second cross-linking, to obtain the pre-loadable dried biological heart valve.

In the present disclosure, it is creative to soak the fresh animal pericardium in an aqueous solution of soluble elastin or glycosaminoglycan, and then the carboxyl group contained in the elastin or glycosaminoglycan is chemically cross-linked with the amino group in the fresh pericardium in the mixed solution of carbodiimide (1-ethyl-3-(3-dimethylaminopropyl)carbodiimide, EDC) or N-hydroxysuccinimide (NHS) to form an amide bond after dehydration condensation. In this way, the elastin or glycosaminoglycan is bound to the pericardium via a chemical bond, whereby the toughness of the biological valve is improved.

In Step S200, the drying is preferably dehydration and drying in an alcohol solvent. More preferably, the pericardium after the second cross-linking is dehydrated and dried over gradient concentrations of an alcohol solvent.

In general, the preparation method of the present disclosure includes: 1. chemical toughening treatment of the biological valve; 2. cross-linking of the biological valve; and 3. drying, where the drying is preferably dehydration and drying in an alcohol solvent. The chemical toughening treatment of the biological valve and the dehydration and drying over gradient concentrations of an alcohol solvent are the key steps in the present disclosure.

Further, the animal pericardium mentioned in the present disclosure includes, but is not limited to, porcine pericardial valves, bovine pericardial valves and the like. In Step S100, before the fresh animal pericardium is soaked in the aqueous solution of soluble elastin or glycosaminoglycan, the method also includes a step of washing the fresh animal pericardium, and the step of washing the fresh animal pericardium includes a cell removal treatment. In an embodiment of washing, fresh porcine or bovine pericardial tissue is collected and stored in a wet state at a low temperature of 4° C. The pericardial tissue is washed with distilled water by gentle friction under a fluid pressure with shaking to remove the attached non-pericardial and non-collagen tissues. The washing in the present disclosure achieves effective cell removal from the pericardial tissue through osmotic shock, and preferably the washing continues until no attached non-pericardial or non-collagen tissue is observed. In an embodiment, preferably, the step of washing the fresh animal pericardium includes: washing the fresh animal pericardium with distilled water at 3 to 5° C. with shaking at 80 to 120 rpm for 1.5 to 3 hrs. For example, the fresh animal pericardium can be washed with distilled water at 4° C. with shaking at 100 rpm for 2 hrs, and then the washed fresh animal (porcine or bovine) pericardium is soaked in an aqueous solution of soluble elastin or glycosaminoglycan.

Further, Step S100 is a chemical toughening treatment process of the biological valve, and the soluble elastin or glycosaminoglycan solution is a solution selected from a group consisting of soluble elastin, hyaluronic acid, chondroitin sulfate, dermatan sulfate, keratan sulfate, heparan sulfate, heparin, and a mixture of any combination thereof. Preferably, the pericardium is soaked for 2 to 24 hrs in a 0.1 to 10 wt % aqueous solution of soluble elastin or glycosaminoglycan at 25 to 37° C. with shaking. This step needs to ensure that the soluble elastin or glycosaminoglycan reaches nearly saturated physical permeation, so as to introduce as much water-soluble elastin or glycosaminoglycan as possible.

Further, in Step S100, the pericardium is subjected to the first cross-linking reaction by soaking in a 0.1 to 1 M mixed solution of carbodiimide oi N-hydroxysuccinimide at 25 to 37° C. with shaking for 2 to 24 hrs. This step will achieve stable chemical cross-linking of the soluble elastin or glycosaminoglycan permeated in the previous step with the pericardial tissue, thereby improving the toughness of the biological valve.

Further, in Step S200, the pericardium after the first cross-linking is subjected to the second cross-linking reaction by soaking in a 0.25 to 1 vol % aqueous glutaraldehyde solution at 25 to 37° C. with shaking for 1 to 7 days. This step will achieve stable cross-linking of most collagen tissues, to improve the structural stability of the entire pericardial tissue, and reduce or eliminate the immunogenicity.

Further, in Step S200, the alcohol solvent includes one or more of methanol, ethanol, isopropanol, glycerol, n-propanol, n-butanol, n-pentanol, n-undecanol, n-dodecanol, 2-propanol, 2-butanol, 2-hexanol, cyelohexanol, and tert-butanol. The alcohol solvent mentioned in the present disclosure may be a mixed solvent, for example, 50% isopropanol or 50% glycerol. 90% isopropanol or 10% glycerol, and the like. Preferably, the pericardium after the second cross-linking is sequentially soaked in 50% isopropanol or 50% glycerol for 20 to 30 hrs (e.g. 24 hrs) and then in 90% isopropanol or 10% glycerol for 20 to 30 hrs (e.g. 24 hrs) at 25 to 37° C. to achieve the gradient dehydration of the biological valve, thereby completing the drying of the biological heart valve.

An embodiment of the present disclosure also provides a pre-loadable dried biological heart valve, which is prepared by the above-mentioned preparation method. The dried biological heart valve prepared by the preparation method of the present disclosure has good toughness and can be quickly flattened in a simulated folding and pressing test.

In the present disclosure, a unique dried valve toughening technology is adopted, so that the prepared dried biological heart valve has good toughness, and can be quickly flattened in a simulated folding and pressing test. The pre-loadable dried biological valve can be preserved without a glutaraldehyde solution. This reduces the residue of glutaraldehyde, reduces the calcification and toxicity caused by glutaraldehyde, simplifies the preoperative mounting of the valve system, and reduces the additional risks of surgery.

The present disclosure is described in detail by way of specific examples as follows.

Example 1

The fresh porcine pericardium was available from a local slaughterhouse. Glutaraldehyde, carbodiimide (EDC) and N-hydroxysuccinimide (NHS) were available from Chengdu Best Reagent Company. The soluble elastin was available from Sigma-Aldrich. The washed porcine pericardium was soaked in a 5% aqueous solution of soluble elastin for 24 hrs, taken out and rinsed. Then the porcine pericardium was cross-linked in a mixed aqueous solution of 0.2 M carbodiimide (EDC) or 0.1 M N-hydroxysuccinimide (NHS) for 2 hrs and washed with distilled water. Then the porcine pericardium was cross-linked in a 0.5% glutaraldehyde aqueous solution (pH 7.4, 25° C.) for 72 hrs, and then washed with distilled water. Subsequently, the porcine pericardium was sequentially soaked in 50% isopropanol or 50% glycerol for 24 hrs and then in 90% isopropanol or 10% glycerol for 24 hrs at 25° C., to achieve the gradient dehydration of the biological valve. A pre-loadable dried biological heart valve with good toughness was obtained.

After test, it is found that the dried biological heart valve prepared in this example can be quickly flattened within five minutes in a simulated folding and pressing test (where the biological heart valve is pressed with a load of 10 kg for 30 days after being folded twice), with good toughness and no obvious folding damage. Uniaxial tensile test (sample size: 1*5 cm) shows that the tensile stress at break is greater than 15 N.

Example 2

The fresh porcine pericardium was available from a local slaughterhouse. Glutaraldehyde, carbodiimide (EDC) and N-hydroxysuccinimide (NHS) were available from Chengdu Best Reagent Company. Hyaluronic acid was available from Shanghai Aladdin Biochemical Technology Co., Ltd. The washed porcine pericardium was soaked in a 5% aqueous solution of hyaluronic acid for 24 hrs, taken out and rinsed. Then the porcine pericardium was cross-linked in a mixed aqueous solution of 0.2 M carbodiimide (EDC) or 0.1 M N-hydroxysuccinimide (NHS) for 2 hrs and washed with distilled water. Then the porcine pericardium was cross-linked in a 0.5% glutaraldehyde aqueous solution (pH 7.4, 25° C.) for 72 hrs, and then washed with distilled water. Subsequently, the porcine pericardium was sequentially soaked in 50% isopropanol or 50% glycerol for 24 hrs and then in 90% isopropanol or 10% glycerol for 24 hrs at 25° C., to achieve the gradient dehydration of the biological valve. A pre-loadable dried biological heart valve with good toughness was obtained.

After test, it is found that the dried biological heart valve prepared in this example can be quickly flattened within five minutes in a simulated folding and pressing test (where the biological heart valve is pressed with a load of 10 kg for 30 days after being folded twice), with good toughness and no obvious folding damage. Uniaxial tensile test (sample size: 1*5 cm) shows that the tensile stress at break is greater than 15 N.

Example 3

The fresh porcine pericardium was available from a local slaughterhouse. Glutaraldehyde, carbodiimide (EDC) and N-hydroxysuccinimide (NHS) were available from Chengdu Best Reagent Company. The soluble elastin was available from Sigma-Aldrich. Hyaluronic acid was available from Shanghai Aladdin Biochemical Technology Co., Ltd. The washed porcine pericardium was soaked in a mixed aqueous solution of 2.5% soluble elastin and 2.5% hyaluronic acid for 24 hrs, taken out and rinsed. Then the porcine pericardium was cross-linked in a mixed aqueous solution of 0.2 M carbodiimide (EDC) or 0.1 M N-hydroxysuccinimide (NHS) for 2 hrs and washed with distilled water. Then the porcine pericardium was cross-linked in a 0.5% glutaraldehyde aqueous solution (pH 7.4, 25° C.) for 72 hrs., and then washed with distilled water. Subsequently, the porcine pericardium was sequentially soaked in 50% isopropanol or 50% glycerol for 24 hrs and then in 90% isopropanol or 10% glycerol for 24 hrs at 25° C., to achieve the gradient dehydration of the biological valve. A pre-loadable dried biological heart valve with good toughness was obtained.

After test, it is found that the dried biological heart valve prepared in this example can be quickly flattened within five minutes in a simulated folding and pressing test (where the biological heart valve is pressed with a load of 10 kg for 30 days after being folded twice), with good toughness and no obvious folding damage. Uniaxial tensile test (sample size: 1*5 cm) shows that the tensile stress at break is greater than 15 N.

Example 4

The fresh porcine pericardium was available from a local slaughterhouse. Glutaraldehyde, carbodiimide (EDC) and N-hydroxysuccinimide (NHS) were available from Chengdu Best Reagent Company. The soluble elastin was available from Sigma-Aldrich. Hyaluronic acid was available from Shanghai Aladdin Biochemical Technology Co., Ltd. The washed porcine pericardium was soaked in a 0.1% aqueous solution of soluble elastin for 24 hrs, taken out and rinsed. Then the porcine pericardium was cross-linked in a mixed aqueous solution of 0.2 M carbodiimide (EDC) or 0.1 M N-hydroxysuccinimide (NHS) for 2 hrs and washed with distilled water. Then the porcine pericardium was cross-linked in a 0.5% glutaraldehyde aqueous solution (pH 7.4, 25° C.) for 72 hrs, and then washed with distilled water. Subsequently, the porcine pericardium was sequentially soaked in 50% isopropanol or 50% glycerol for 24 hrs and then in 90% isopropanol or 10% glycerol for 24 hrs at 25° C., to achieve the gradient dehydration of the biological valve. A pre-loadable dried biological heart valve with good toughness was obtained.

After test, it is found that the dried biological heart valve prepared in this example can be quickly flattened within five minutes in a simulated folding and pressing test (where the biological heart valve is pressed with a load of 10 kg for 30 days after being folded twice), with good toughness and no obvious folding damage. Uniaxial tensile test (sample size: 1*5 cm) shows that the tensile stress at break is greater than 15 N.

Example 5

The fresh porcine pericardium was available from a local slaughterhouse. Glutaraldehyde, carbodiimide (EDC) and N-hydroxysuccinimide (NHS) were available from Chengdu Best Reagent Company. The soluble elastin was available from Sigma-Aldrich. Hyaluronic acid was available from Shanghai Aladdin Biochemical Technology Co., Ltd. The washed porcine pericardium was soaked in a 10% aqueous solution of soluble elastin for 24 hrs, taken out and rinsed. Then the porcine pericardium was cross-linked in a mixed aqueous solution of 0.2 M carbodiimide (EDC) or 0.1 M N-hydroxysuccinimide (NHS) for 2 hrs and washed with distilled water. Then the porcine pericardium was cross-linked in a 0.5% glutaraldehyde aqueous solution (pH 7.4, 25° C.) for 72 hrs, and then washed with distilled water. Subsequently, the porcine pericardium was sequentially soaked in 50% isopropanol or 50% glycerol for 24 hrs and then in 90% isopropanol or 10% glycerol for 24 hrs at 25° C., to achieve the gradient dehydration of the biological valve. A pre-loadable dried biological heart valve with good toughness was obtained.

After test, it is found that the dried biological heart valve prepared in this example can be quickly flattened within five minutes in a simulated folding and pressing test (where the biological heart valve is pressed with a load of 10 kg for 30 days after being folded twice), with good toughness and no obvious folding damage. Uniaxial tensile test (sample size: 1*5 cm) shows that the tensile stress at break is greater than 15 N.

Example 6

The fresh porcine pericardium was available from a local slaughterhouse. Glutaraldehyde, carbodiimide (EDC) and N-hydroxysuccinimide (NHS) were available from Chengdu Best Reagent Company. The soluble elastin was available from Sigma-Aldrich. Hyaluronic acid was available from Shanghai Aladdin Biochemical Technology Co., Ltd. The washed porcine pericardium was soaked in an aqueous solution of 2.5% soluble elastin, hyaluronic acid, and chondroitin sulfate for 24 hrs, taken out and rinsed. Then the porcine pericardium was cross-linked in a mixed aqueous solution of 0.2 M carbodiimide (EDC) or 0.1 M N-hydroxysuccinimide (NHS) for 2 hrs and washed with distilled water. Then the porcine pericardium was cross-linked in a 0.5% glutaraldehyde aqueous solution (pH 7.4, 25° C.) for 72 hrs., and then washed with distilled water. Subsequently, the porcine pericardium was sequentially soaked in 50% isopropanol or 50% glycerol for 24 hrs and then in 90% isopropanol or 10% glycerol for 24 hrs at 25° C., to achieve the gradient dehydration of the biological valve. A pre-loadable dried biological heart valve with good toughness was obtained.

After test, it is found that the dried biological heart valve prepared in this example can be quickly flattened within five minutes in a simulated folding and pressing test (where the biological heart valve is pressed with a load of 10 kg for 30 days after being folded twice), with good toughness and no obvious folding damage. Uniaxial tensile test (sample size: 1*5 cm) shows that the tensile stress at break is greater than 15 N.

In summary, the present disclosure provides a pre-loadable dried biological heart valve and a preparation method thereof. The dried biological heart valve prepared by the preparation method of the present disclosure has good toughness and can be quickly flattened in a simulated folding and pressing test. The pre-loadable dried biological valve can be preserved without a glutaraldehyde solution. This reduces the residue of glutaraldehyde, reduces the calcification and toxicity caused by glutaraldehyde, simplifies the preoperative mounting of the valve system, and reduces the additional risks of surgery.

It is to be understood that the present disclosure is not limited to the above embodiments, modifications and variations can be made by those skilled in the art in accordance with the above description, which shall be covered in the protection scope of the appended claims.

What is claimed is:

1. A method for preparing a pre-loadable dried biological heart valve, comprising:
    Step A: soaking a fresh animal pericardium in an aqueous solution of soluble elastin or glycosaminoglycan, and then subjecting the pericardium to a first cross-linking reaction in a mixed solution of carbodiimide or N-hydroxysuccinimide to allow the soluble elastin or glycosaminoglycan to bind to the pericardium via a chemical bond; and
    Step B: subjecting the pericardium after the first cross-linking to a second cross-linking reaction in an aqueous glutaraldehyde solution, and then drying the pericardium after the second cross-linking, to obtain the pre-loadable dried biological heart valve.

2. The method for preparing a pre-loadable dried biological heart valve according to claim 1, wherein in Step A, the pericardium is soaked for 2 to 24 hrs in a 0.1 to 10 wt % aqueous solution of soluble elastin or glycosaminoglycan at 25 to 37° C. with shaking.

3. The method for preparing a pre-loadable dried biological heart valve according to claim 1, wherein in Step A, the pericardium is subjected to the first cross-linking reaction by soaking in a 0.1 to 1 M mixed solution of carbodiimide or N-hydroxysuccinimide at 25 to 37° C. with shaking for 2 to 24 hrs.

4. The method for preparing a pre-loadable dried biological heart valve according to claim 1, wherein in Step B, the pericardium after the first cross-linking is subjected to cross-linking reaction by soaking in a 0.25 to 1 vol % aqueous glutaraldehyde solution at 25 to 37° C. with shaking for 1 to 7 days.

5. The method for preparing a pre-loadable dried biological heart valve according to claim 1, wherein in Step B, the drying is dehydration and drying in an alcohol solvent.

6. The method for preparing a pre-loadable dried biological heart valve according to claim 5, wherein in Step B, the pericardium after the second cross-linking is dehydrated and dried over gradient concentrations of an alcohol solvent.

7. The method for preparing a pre-loadable dried biological heart valve according to claim 5, wherein in Step B, the alcohol solvent comprises one or more of methanol, ethanol, isopropanol, glycerol, n-propanol, n-butanol, n-pentanol, n-undecanol, n-dodecanol, 2-propanol, 2-butanol, 2-hexanol, cyclohexanol and tert-butanol.

8. The method for preparing a pre-loadable dried biological heart valve according to claim 6, wherein in Step B, the pericardium after the secondary crosslinking is sequentially soaked in 50% isopropanol or 50% glycerol for 20-30 hrs, and then in 90% isopropanol or 10% glycerol for 20 to 30 hrs at 25 to 37° C. to accomplish the dehydration and drying.

9. The method for preparing a pre-loadable dried biological heart valve according to claim 1, wherein in Step A, the soluble elastin or glycosaminoglycan solution is selected from a group consisting of: soluble elastin, hyaluronic acid, chondroitin sulfate, dermatan sulfate, keratan sulfate, heparan sulfate, heparin, and a mixture of any combination thereof.

10. The method for preparing a pre-loadable dried biological heart valve according to claim 1, wherein in Step A, the method further comprises a step of washing the fresh animal pericardium before soaking the fresh animal pericardium in the aqueous solution of soluble elastin or glycosaminoglycan.

11. The method for preparing a pre-loadable dried biological heart valve according to claim 10, wherein the step of washing the fresh animal pericardium comprises washing the fresh animal pericardium with distilled water at 3 to 5° C. with shaking at 80 to 120 rpm for 1.5 to 3 hrs.

12. The method for preparing a pre-loadable dried biological heart valve according to claim 10, wherein the step of washing the fresh animal pericardium comprises a cell removal treatment.

13. A pre-loadable dried biological heart valve, prepared by the method according to claim 1.

* * * * *